United States Patent [19]

Jensen et al.

[11] 4,007,368
[45] Feb. 8, 1977

[54] HEATING APPARATUS

[75] Inventors: Robert A. Jensen, Hazel Crest; John A. Tesk, Woodridge; Daniel Odulio, Chicago, all of Ill.

[73] Assignee: Howmedica, Inc.

[22] Filed: Jan. 10, 1975

[21] Appl. No.: 540,178

[52] U.S. Cl. .................................... 219/388; 34/1; 34/236; 99/386; 432/121
[51] Int. Cl.² .......................................... F27B 9/06
[58] Field of Search ................. 219/388; 34/1, 201, 34/236; 432/121; 99/386, 443 R, 443 C

[56] References Cited
UNITED STATES PATENTS

| | | | |
|---|---|---|---|
| 1,656,709 | 1/1928 | Kelly | 219/388 |
| 2,575,426 | 11/1951 | Parnell | 219/388 X |
| 3,448,678 | 6/1969 | Burstein | 99/386 |
| 3,537,185 | 11/1970 | Ingram | 34/1 |

Primary Examiner—Volodymyr Y. Mayewsky
Attorney, Agent, or Firm—Pennie & Edmonds

[57] ABSTRACT

A heating apparatus is disclosed. The heating apparatus, adapted for use in the manufacture of a dental product, is formed by an enclosure having a heated zone and a control area. Layers of insulation enclose the heated zone. A conveyor is disposed in the heated zone for moving the dental product to be treated through a temperature gradient. An infinite switch within the control area is adjustable to vary the speed of the conveyor. Further controls within the area energize the apparatus and permit alarm functions.

4 Claims, 4 Drawing Figures

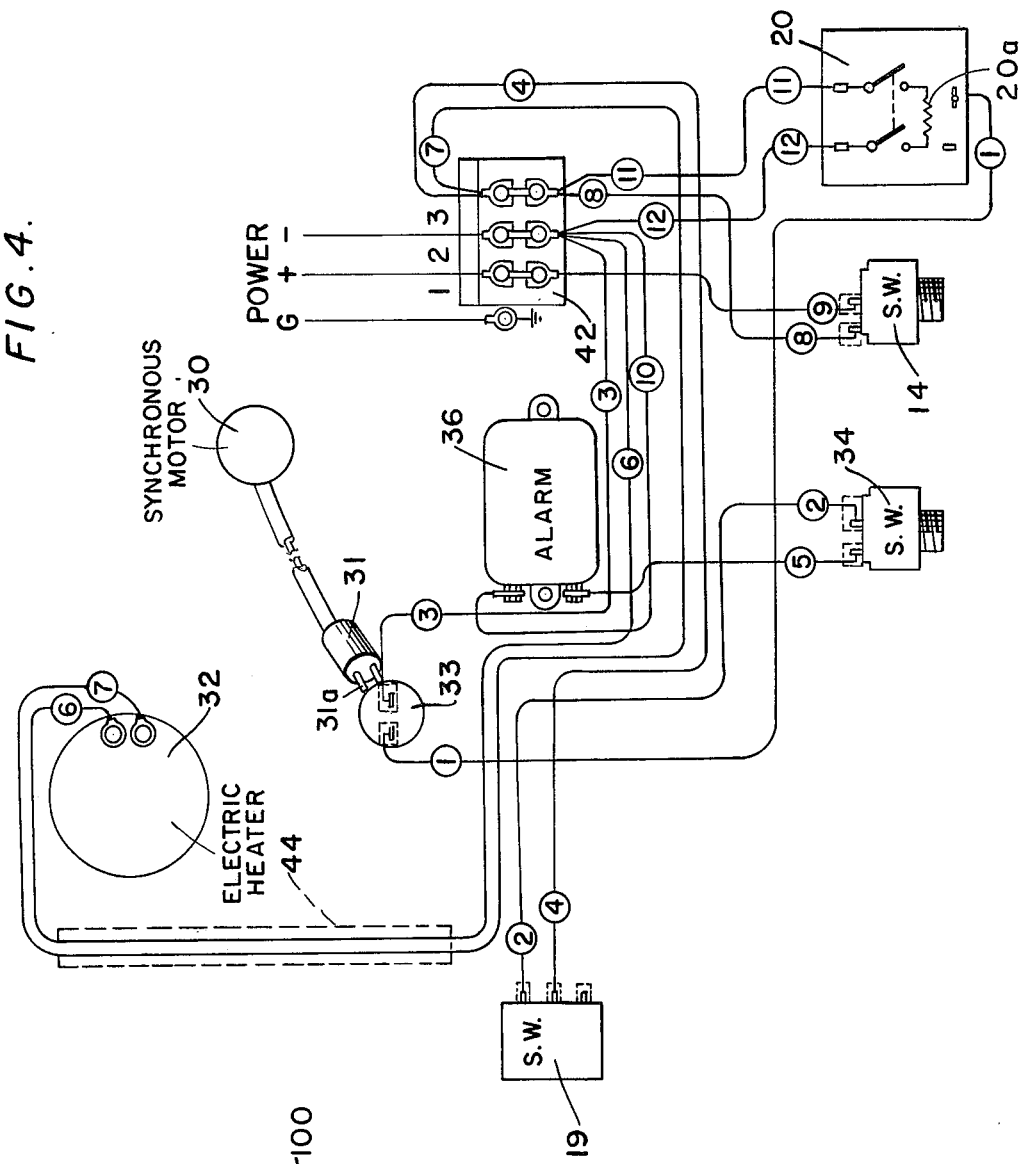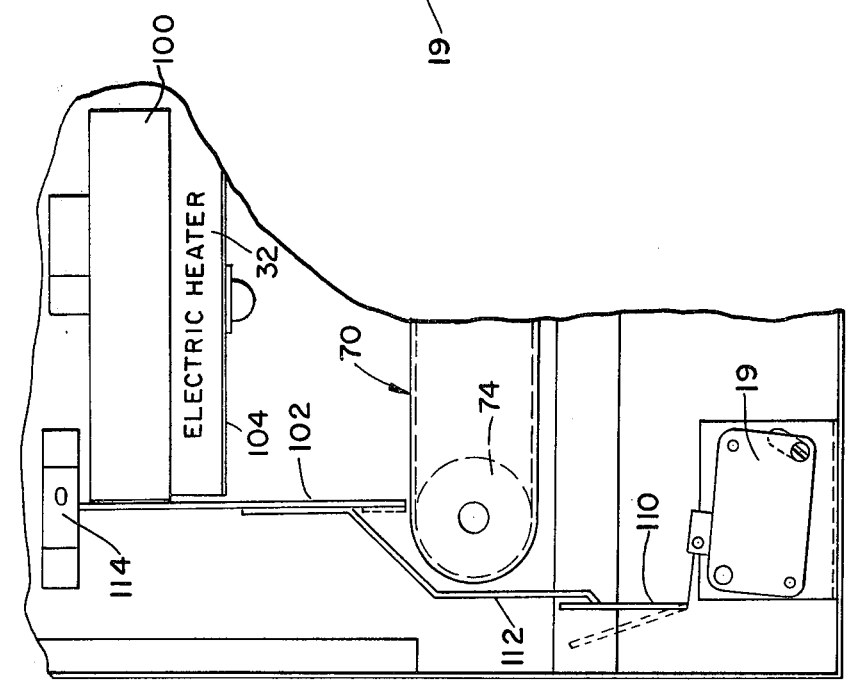

HEATING APPARATUS

BACKGROUND OF THE INVENTION

Non-custom ceramic dental products such as artificial teeth are readily available from commercial manufacturing sources for use in the fabrication of intra-oral restorative devices. However, there are a number of types of ceramic dental products which require individual custom-type production to satisfy certain requirements for an individual patient. One such product includes ceramic jacket crowns which generally are fabricated by a multi-layered build-up technique on a metal substrate, the individual layers of which must be dried and successively fired before the application of the next outer layer.

Further types of ceramic dental products including porcelain facings, veneers, porcelain bridges, porcelain inlays, and various other porcelain dental products are also generally fabricated by a successive step technique in which a layer is applied to a base member of suitable type and fired. Thereupon, additional layers are applied and fired. In this manner a finished product of required shape, shade or color, and dimension for particular use in a restorative device may be fabricated.

Each of the porcelain layers usually are applied in the form of a slurry, which is somewhat paste-like. The slurry is then dried, prior to being fused or fired, to remove moisture from the condensed porcelain thereby substantially to obviate the possibility that the porcelain will explode from the metal substrate during fusing or firing. Preferably, heat is used to finish the drying of the applied slurry layer as rapidly as possible so as to conserve the amount of time required to complete the ceramic dental product.

The drying of such applied layers may be carried out in the same or different furnace from that in which firing or vitrification of the various layers occurs. In the former case the final firing temperature usually is not applied until satisfactory evacuation of the product has occurred. Satisfactory evacuation of the product has in the past been the result of "guesstimation," albeit educated "guesstimation." To this end, the coated metal substrate or crown generally is placed within and spaced from the open door of the furnace by a distance of a couple of inches. Over a period of time the crown is moved closer to the door until it is considered that the crown has been sufficiently dried. At this time the crown is repositioned to the rear of the furnace and subjected to a greater temperature to accomplish a fusing or firing of the crown.

This procedure, while it may be carried out successfully by trained personnel, leaves something to be desired from the standpoint of the overall manufacturing procedure. Even if trained personnel are utilized at this stage of the operation, distraction because of other duties may result in inconsistency of product, a result of variation in time during which the drying operation is carried out. As already discussed, a crown which is improperly dried, i.e., one not dried sufficiently, may explode from or crack on the metal substrate when subjected to firing temperature. On the other hand, if the crown is dried for too long a period it may begin to bisque bake and upon full firing attain an incorrect opacity (transparency) or an undesirable color. If during the initial drying period which may continue for a period of time longer than desired the drying temperature is at or near to a temperature within the firing range the porcelain may flake off upon movement into the firing furnace.

The above procedure of drying a crown is not compatible with production efficiency. If the operator's time is consumed by the necessity both of checking product and determining through past experience whether suitable drying of the product has been carried out that operator may not be able adequately to carry out other tasks which will serve as a distraction from the principal endeavor.

BRIEF DESCRIPTION OF THE INVENTION

The present invention seeks to overcome the aforementioned problems which exist in fabrication of dental prothesis in the dental laboratory. To this end the present invention is directed to a heating furnace into which a crown may be placed for drying or evaporation of the moisture content from the condensed porcelain and from which the crown after having been properly dried may be removed for further processing.

In one aspect the present invention is directed to a heating furnace construction providing a controlled temperature gradient between a first or cool end and a second or heated end. To this end a heating unit is disposed at one end of a heated and insulated enclosure. The heater is of a type to provide controlled heating requirements. A conveyor is disposed for movement within the furnace enclosure thereby to pass each crown from the first to a second end permitting during travel drying of the moisture content from the condensed porcelain.

As a second aspect of the present invention the conveyor may be controlled within limits to vary the speed of movement of the crown through the temperature gradient. The speed of movement of the conveyor and accordingly the crown thereon is adjusted to permit adequate drying of the porcelain layer. A crown having a very wet, heavy build-up of porcelain will require a proportionately longer heating cycle than will a thinly condensed layer. Thus, a thinly condensed layer may require a traverse time of from three to four or five minutes for drying; whereas, a crown having a wet, heavy build-up of porcelain may require a longer traverse time of for example seven or more minutes for drying. The motor control is carried out through adjustment of an infinite switch.

In a further aspect the present invention provides a limit control at the end of the conveyor within the heated zone for the purpose of stopping the movement of the crown. As a second function, the limit control may energize an alarm which will advise the operator that the crown has reached the heated end of the furnace and that it may immediately be transferred to the furnace to be fired.

The limit control may take the form of a touch sensitive wall disposed at the end of the conveyor track. The wall may be formed by the switch arm control of a micro-switch.

The furnace of the present invention provides an accurate time/temperature cycle thereby to eliminate problems which occur in firing because of the crown and particularly the porcelain coating being subjected to too short or too long a drying time. The furnace is capable of providing a gradient toward the heated end which may be heated from approximately 600° F. to approximately 650° F. This temperature is sufficiently high to carry out the requirements of the process. However, the temperature is not high enough so that product which is not immediately removed upon the occurrence of the alarm signal will be subjected to the possible dangers of firing or overdrying. Further, the furnace of the present invention permits the operator to carry out additional process functions. Production is enhanced.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended thereto. Those skilled in the art will appreciate that the conception upon which this disclosure is based may readily be utilized as a basis for the designing of other structures for carrying out the several purposes of the invention. It is important, therefore, that the claims be regarded as including such equivalent construction as do not depart from the spirit and scope of the invention.

DESCRIPTION OF THE DRAWINGS

The accompanying drawings form a part of the present application. By these drawings which illustrate a preferred form of the invention;

FIG. 3 is a partial view of the interior of the housing illustrating the end of the conveyor run and a switch which is actuated by product arriving at the conveyor travel limit; and FIG. 4 is a wiring and schematic diagram of the preheater assembly.

DESCRIPTION OF THE PREFERRED EMBODIMENT

Figure 1:
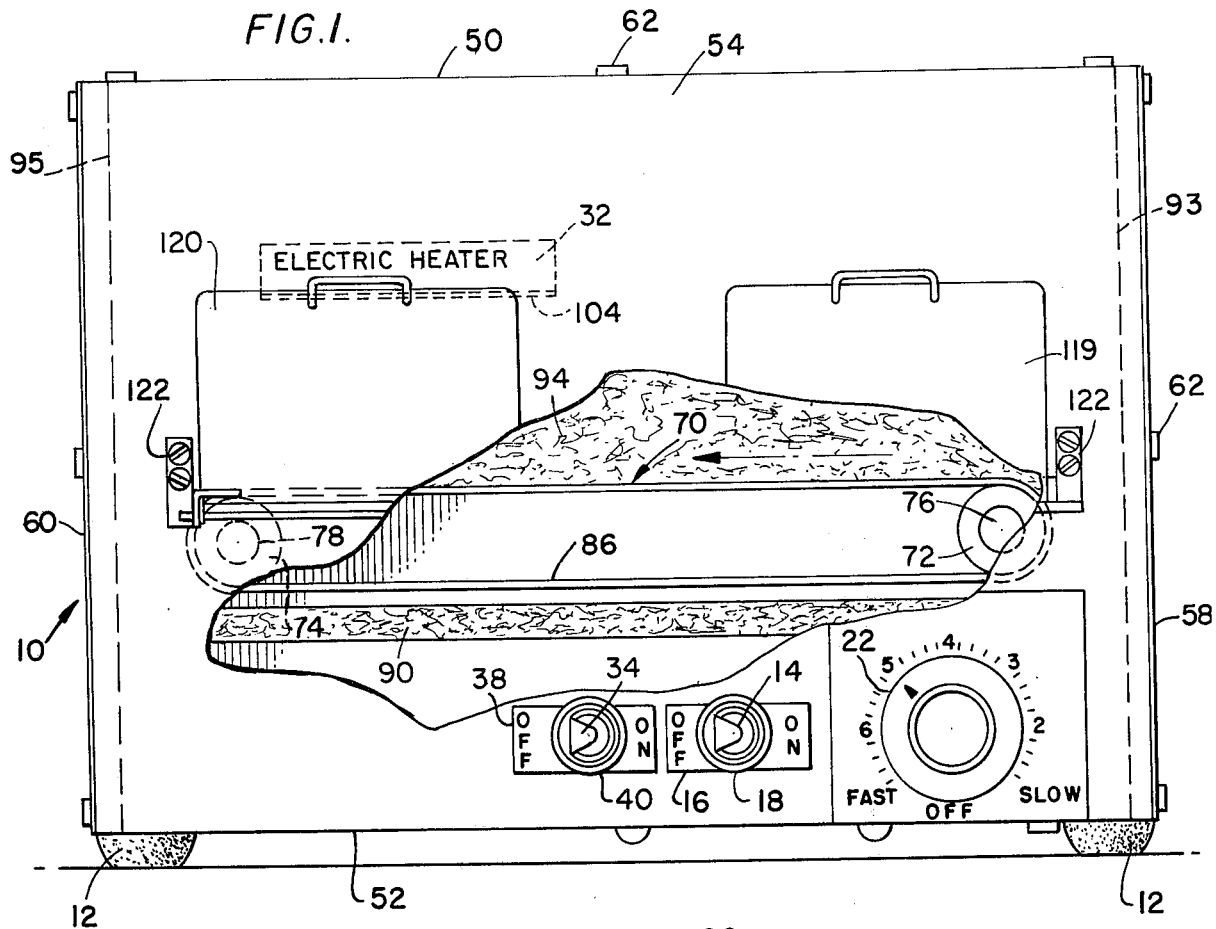
FIG. 1 is a front elevation of the preheater furnace assembly having a portion of the housing wall broken away to illustrate a conveyor within a heated enclosure.

The preheater furnace assembly includes housing 10 which is formed by a plurality of walls defining a closed space therein. The housing may be supported on a surface by feet 12.

As discussed, the preheater furnace assembly provides generally a housing having a heated zone defined by insulative layers adjacent the front and rear, end and top walls of the housing and a lower insulative layer separating the heated zone from a lower control area. A heater is located within the heated zone toward one side of the housing for the purpose of heating the same. A conveyor is also located within the heated zone and provides a run from a cool to a heated location in the vicinity of the heater. The conveyor may be driven at an adjustable controlled speed to move a crown or bridge along a run. Various switching means are disposed within the control area. The switching means provide an "On-Off" control for the assembly, a variable control for the motor, and, if desired, an alarm function which may be activated to notify the operator that the crown or bridge has moved through the heated zone.

The operation of the preheater furnace assembly may be appreciated from the following discussion with reference particularly to FIG. 4. The operation is primarily controlled by toggle switch 14 serving as the main power switch and secondarily controlled by an infinite switch 20. The infinite switch is in one series connection with the toggle switch 14. The toggle switch is secured to the front wall of housing 10 by hardware 16 (including "On-Off" indication) and facenut 18; whereas the infinite switch is secured between the front and rear wall of the housing. The infinite switch carries a dial 22 and a knob for control which is movable from an "Off" and through positions designated as "Slow" and "Fast." Adjustment of the dial knob to a predetermined dial set position adjusts the speed of movement of the conveyor. In this manner the conveyed product may be conveyed through the heated zone within a period of time up to as many as approximately twenty minutes or more.

A microswitch 19 is normally open at the conductors 2 and 4 in the illustrated circuit arrangement. The purpose of the microswitch 19 will become apparent as the description continues.

Assuming the infinite switch 20 to be in the "On" condition, operation of toggle switch 14 serves to energize motor 30 of the synchronous type. The motor through suitable plug means 31 including plug contacts 31a is connected to socket 33 and in the line of conductors 1 and 3. The motor is the prime mover for the conveyor, to be discussed. A heater 32 is controlled directly by toggle switch 14. Thus, upon operation of the assembly the heater will energize and continue the heating process until turned "Off."

Heater 32 may be of the ceramic base type and capable of developing approximately 240W. heating capacity. Preferably, the heater will be disposed adjacent one end of the housing and mounted for upside down use. As seen in the figures the heat emanating surface extends throughout at least a major portion of the width and along a portion of the length of the conveyor from adjacent the left end of housing 10. Thereby, during a period of operation the heater will create a temperature gradient toward the heated area. Insulation and maintenance of the heated environment within the enclosure is provided by a layer of vermiculite and/or asbestos insulating material.

A further toggle switch 34 controls the alarm function which may be audible or visual, or a combination of both, as desired. The alarm toggle switch 34 is carried on the front face of the housing and supported by hardware 38 and facenut 40 in the manner of support of toggle switch 14. In the present embodiment the alarm is illustrated as being a buzzer 36.

A power source of 115V, 60Hz is connected to a terminal plate 42. The connector is in the form of a two conductor with ground cable. Toggle switch 14 in the "On" condition closes the circuit to the heater 32 through the series connection provided by conductors 6-9 between points 1 and 2 on terminal plate 42. As shown in the wiring schematic the conductors 6–7 in the vicinity of the heater are shielded by glass braid tubing 44.

The infinite switch 20 provides the "On-Off" and speed control of motor 30. Therefore, the motor drives at the speed set by dial 22 on the housing face. The drive of motor 30 is continuous. Thus, as the dial 22 of the infinite switch 20 is rotated counterclockwise (see FIG. 1) from the "Off" position the ganged switches in lines 11 and 12 close and a tap (not shown) in line 1 moves along the resistor 20a from a position adjacent the right end to a position adjacent the left end of the resistor as the dial is rotated in a further counterclockwise direction for purposes of reducing the output speed of motor 30. When the crown or bridge product arrives at the limit of conveyor travel its forward impetus will cause an actuator plate carried by an operating lever or arm of microswitch 19 to pivot and close the normally open microswitch 19. If the toggle switch 34 is set to "On" the buzzer 36 will be energized through the circuit conductors 2, 5 and 10.

Figure 2:
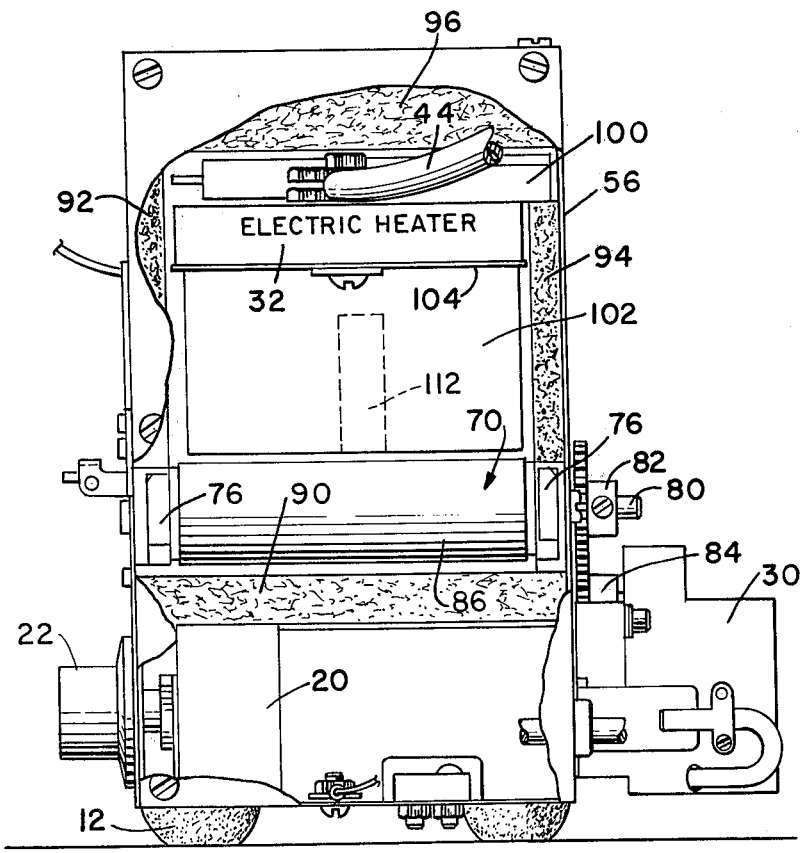
FIG. 2 is a right end elevation of the preheater furnace assembly (reference being with regard to FIG. 1), again, having a portion of the wall broken away to illustrate the heated enclosure, the conveyor and the heater within.

Referring now to FIGS. 1-3, the housing or chassis 10 is formed by a plurality of walls including a top and bottom walls 50, 52, front and rear walls 54, 56, and end walls 58, 60. The walls may be mounted together by any means and held by screws 62. The walls of the housing are formed preferably of cold rolled steel which may be approximately 22 gauge (0.030 inches thick).

A conveyor assembly 70 is supported for movement within the upper space of the housing. The conveyor assembly provides a pair of spaced rolls including an idler roll 72 and a driven roll 74. The rolls are supported by a pair of opposed spindle members 76, 78 respectively. The spindle members are connected to the rolls and, in turn, rotate within openings of spaced bearing members which provide a journal. The roll 74 includes a roll shaft 80 which is press fit within the spindle member 78. The roll shaft extends from the housing for driving connection to motor 30. To this end, a pinion gear 82 is secured such as by keyed securement to roll shaft. The pinion is disposed to be directly driven by the sprocket gear 84 at the output of motor 30. As indicated, the motor is controlled by the infinite switch 20 and drives at a variable speed as determined by the setting of the switch.

A conveyor belt 86 is trained about the idler and driven rolls 72, 74 for movement of a dental product carried thereon in the direction illustrated by the arrow in FIG. 1. Movement of the dental product is from one side of the chamber toward the other side within the region below the heater located as illustrated in the figures. The idler roll and driven roll, if desired, is adjustable thereby to retain the belt 86 in tension. To this end, the bearings supporting the idler roll 72 may be supported by and movable within a slot of a conveyor weldment (not shown) carried by the housing. Any convenient assemblage of structure as well known may be employed. Similar structure may be employed for cooperation with the driven roll for adjustment of the same. The belt may be formed of stainless steel member whose ends are joined by spot welding.

The conveyor is disposed in the upper heated area and forms, with an insulation layer 90, the demarcation of the control area and heated environment. The layer of insulation is formed of vermiculite or asbestos millboard or a combination thereof. Further similar layers 92, 93, 94, 95 and 96 of insulation are supported within the housing. These layers respectively, are supported by the front, right side, rear, left side, and top walls of the chassis.

The heater 32 is supported by the mounting bracket 100 to the left of the housing as seen in FIGS. 2 and 3. The heater is oriented over the conveyor within the enclosed space bounded by the insulative layers at the top and sides, the conveyor and insulative layer at the bottom, as well as the end layers of insulation and wall or actuation plate 102. A mica sheet 104 forming a heater cover is secured to the underside of the heater 32.

The microswitch 19 is disposed in the control area below the heater. The microswitch has a switch operating arm 110. An actuator lever 112 is connected to the actuator plate 102 and movable with movement of the actuator plate about pivot 114 to actuate the switch 19. As indicated, the actuation of switch 19 to the closed position enables the sounding of the alarm 36, if the operator of toggle switch 34 is in the "On" position.

In operation, a bridge or crown is received on the conveyor 70 for movement toward the heated zone. Preferably, the heater will have been "On" for a period of time necessary to bring the temperature at a point directly below the center of the heater and approximately ½ inch above the conveyor to between 600° F. and 650° F. A door 119 disposed at the right side of the housing (see FIG. 1) provides entry to the enclosed space within the heated zone. The speed of the conveyor is chosen so that necessary predrying is accomplished. At the end of the conveyor run the alarm will sound and the crown or bridge, physically impeded by the actuator plate in continued forward movement with the conveyor after reaching the other side of the chamber, may be removed through a door 120 likewise disposed in the front of the housing to the left of the door 119. Each door is mounted by hinges 122 carried by wall 54. Thus, the door at the right of the housing permits placement of a dental product on the conveyor, while the door at the left of the housing permits removal of the dental product from the conveyor.

Moisture which is removed from the condensed porcelain during the controlled heating of the crown or bridge may be passed out of the heating furnace through either the door 119 or 120 when the preheated crown or bridge is removed from or a crown or bridge to be preheated is placed in the heated area or by other conventional means (not shown) as are well known in the industry. To this end, while the heated area will have some moisture content the size of the housing within which the crown or bridge is subjected to controlled heating is large compared to the amount of moisture removed from the condensed porcelain slurry on the substrate whereby the moisture will readily pass from within the enclosure.

From the foregoing, it will be seen that in accordance with the present invention there is provided a preheater furnace assembly for predrying a porcelain slurry coating condensed on a metallic substrate of a bridge or crown construction. The furnace assembly provides an enclosure and a heated insulated space therein. A conveyor is supported within the space for moving product toward and through a gradient provided for a heater apparatus. The conveyor is movable at a variable controlled speed so that product may be thoroughly predried before introduction to a firing furnace. An alarm sounds when the product has been conveyed from one end of the space to the other end. The operation is such to overcome the heretofore noted problems in the fabrication of dental prothesis and provide advantages heretofore not achieved in similar type devices.

Having described the invention with particular reference to the preferred form thereof it will be obvious to those skilled in the art to which the invention pertains after understanding the invention that various changes and modifications may be made therein without departing from the spirit and scope of the invention defined by the claims appended hereto.

We claim:

1. Apparatus for preheating and reducing the moisture content of dental products before a firing heating comprising a housing having a chamber therein, an endless conveyor track and means for supporting said conveyor track within said housing whereby the run of said conveyor track is substantially from one side of said chamber to the other, drive means and means coupling the output of said drive means to said conveyor track support means for moving said dental products on said conveyor track from said one side of said chamber to said other side, door means in said housing providing access to said chamber within the region adjacent said sides whereby dental products may be located on said conveyor track at said one side of said chamber and removed from said conveyor track at said other side of said chamber, insulating means for said chamber, said insulating means including an insulating layer below said conveyor track dividing said chamber into a heating and a control portion, heating means disposed within said heating portion of said chamber, said heating means having a heat emanating surface within the region of said chamber other side throughout at least a major portion of the width and along a portion of the length of said endless conveyor track, control means supported within said control portion of said chamber, said control means comprising means for connection to an electrical power source and circuit means including said drive means and electrical heating means in parallel connection across said connection means and power source, said circuit means including a first switch means for providing primary control of said drive and heating means, second switch means in said circuit secondarily controlling said drive means; and means within said chamber at said other side for physically impeding forward movement of said dental products as said conveyor track is driven by said drive means, said impeding means being movable slightly upon contact of said dental products whereby said impeding means is adapted to activate a switch which enables operation of an alarm whereby an operator will be advised that said dental products have been conveyed to said other side of said chamber.

2. The apparatus of claim 1 further including alarm means, an alarm switch means capable of actuation when said dental product reaches said other side of said chamber, an alarm switch actuator, and means mechanically connecting said alarm switch actuator and said impeding means whereby said slight movement of said impeding means actuates said alarm switch means.

3. The apparatus of claim 1 wherein said electrical heating means is disposed above said conveyor track at said other side of said chamber for heating the space above said conveyor track and below said heating means to a predetermined temperature.

4. The apparatus of claim 1 wherein said second switch means is infinitely adjustable to control the speed of said conveyor track and movement of products through said heating portion.

* * * * *